Figure 1:
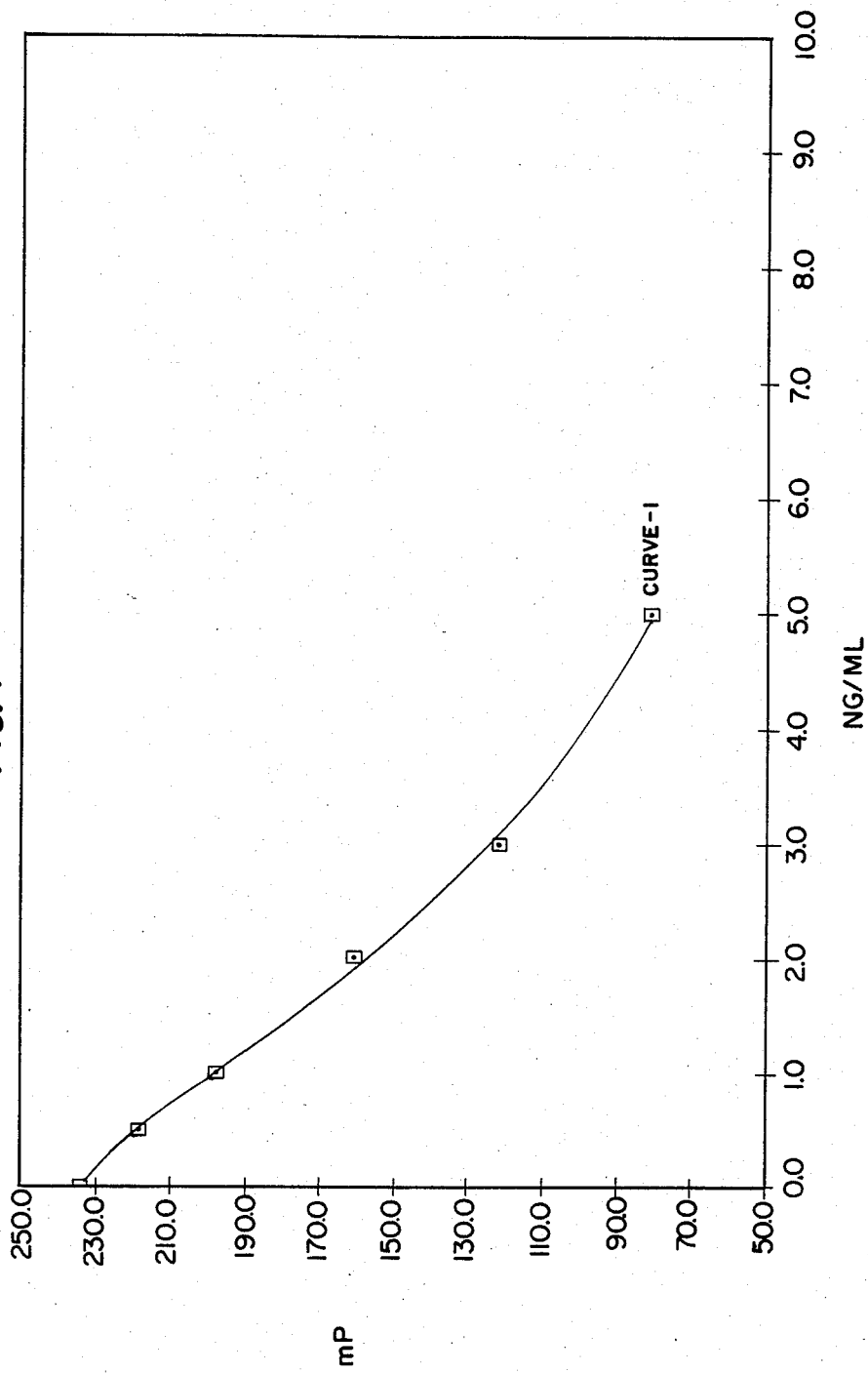

United States Patent [19]

Farrenkopf et al.

[11] Patent Number: 4,698,315

[45] Date of Patent: Oct. 6, 1987

[54] METHOD AND KIT FOR DETERMINING TOTAL DIGOXIN LEVELS INVOLVING AGENT TO DISSOCIATE DIGOXIN-PROTEIN COMPLEX

[75] Inventors: Bruce C. Farrenkopf, Clifton; Richard A. Kaufman, Belleville, both of N.J.

[73] Assignee: Hoffmann-La Roche Inc., Nutley, N.J.

[21] Appl. No.: 726,255

[22] Filed: Apr. 22, 1985

[51] Int. Cl.$^4$ .................. G01N 33/53; G01N 33/533; G01N 33/536; G01N 33/542

[52] U.S. Cl. ...................................... 436/536; 436/63; 436/172; 436/177; 436/537; 436/546; 436/808; 436/815; 436/825

[58] Field of Search ............... 436/536, 537, 546, 808, 436/815, 825, 63, 177, 172

[56] References Cited

U.S. PATENT DOCUMENTS 4,056,468  11/1977  Breiter .
4,492,762   1/1985  Wang ................................. 436/537

FOREIGN PATENT DOCUMENTS 108403   5/1984  European Pat. Off. .
115332   8/1984  European Pat. Off. .
3205506  2/1982  Fed. Rep. of Germany .
3230527  8/1982  Fed. Rep. of Germany .

OTHER PUBLICATIONS

Chemical Abstracts, I, 102:17014e (1985).
Chemical Abstracts, II, 102:89,585q (1985).
Scherrman, J. M. et al., Clin. Chem., 30(2), 337-338 (1984).
Pudek, M. R. et al., Clin. Chem., 29(11), 1972-1974 (1983).

Primary Examiner—Sidney Marantz
Attorney, Agent, or Firm—Jon S. Saxe; George M. Gould; Julie M. Prlina

[57] ABSTRACT

A method for determining total digoxin levels in a biological fluid sample containing digoxin-protein complex which method comprises disrupting the digoxin-protein complex by treating said sample solution with an effective amount of a dissociation agent selected from one or more members of the group consisting of a $C_3$-$C_{26}$ saturated or unsaturated fatty acid, a $C_{2-7}$ lower alkanol, quinidine and α-tocopherol so as to release the bound digoxin from serum protein, passing the treated sample solution through a centrifugal ultrafilter so as to selectively pass digoxin containing sample solution through said filter and retaining said serum proteins and determining the digoxin contents in said sample solution in a fluorescence polarization assay. A kit for carrying out the method is provided.

11 Claims, 1 Drawing Figure

METHOD AND KIT FOR DETERMINING TOTAL DIGOXIN LEVELS INVOLVING AGENT TO DISSOCIATE DIGOXIN-PROTEIN COMPLEX

BACKGROUND

For an assay to be accurate, where the analyte concentration is read off a standard curve, the standards and patient samples must behave indentically in the assay. Perhaps one of the most critical factors between the standards and the patient samples is that the recovery of analyte from the standards must be identical to the recovery of the analyte from the patient samples or erroneous values will result. This is particularly true if the total quantity of analyte in the patient sample is being measured.

In fluorescent polarizaton assays of analytes in serum, one of the undesirable features of this methodology is the high fluorescence background of the serum. This becomes particularly troublesome when low levels of analytes like digoxin are being measured. In this case, the assay is not feasible using serum directly with a fluorescein-labeled digoxin tracer since the serum background fluorescence far exceeds the fluorescence signal emitted by the fluorescein-labeled digoxin tracer.

In order to overcome the high background fluorescence of the serum, protein-free filtrates have typically been made using perchloric or trichloroacetic acids. Although the methods are effective in producing a protein-free filtrate relatively free of background fluorescence, they suffer from other disadvantages. In the case of digoxin, relatively poor recovery is obtained in the supernatant, and in addition the recovery is dependent on the protein concentration in the sample. See for example Porter et al., Clin. Chem. 30, 1826–1829 (1984).

The use of ultrafiltration to produce protein-free filtrates is also known in the art. In such a system, protein becomes selectively partitioned into a fraction of the sample volume (retentate) while free ligand passes essentially unhindered through the membrane along with solvent into the ultrafiltrate. Systems for carrying out such ultrafiltration are commercially available. One such system is the Centrifree TM micropartition system sold by Amicon Corporation located in Danvers, Mass. This is basically a self-contained filter device with a filter membrane of such porosity that about 99.9% of the proteins in serum are prevented from passing through upon centrifugal filtration. The promotional literature accompanying the filters suggest they are to be used for separating "free" serum analytes, particularly drugs, from the protein bound fraction. Thus, in the absence of a dissociating agent to free drug bound to protein, only the free drug in serum would be allowed to pass through the filter and thus be measured in an assay.

Reports in the literature suggest that about 20 to 30% of digoxin in serum is bound to serum proteins. See Pribor et al., Drug Monitoring and Pharmokinetic Data, Pathotex Publishers, Park Forrest South, Ill., p. 57 (1980). Thus, if $^3$H-digoxin were added to human serum, about 70 to 80% of the label would be expected to be recovered in the filtrate. Using 10 normal human sera samples to which $^3$H-digoxin was added, followed by centrifugal filtration through the ultrafilters; it was found that 15 to 25% of the digoxin in these sera could not be recovered in the filtrate and was thus presumably protein bound.

SUMMARY OF THE INVENTION

The present invention relates to an assay for measuring total serum digoxin using a combination of centrifugal ultrafiltration and dissociation agents used to dissociate the digoxin bound to the serum proteins. A number of compounds have been found to be effective either alone or in combination in dissociating protein-bound digoxin from the serum proteins. Examples of such effective dissociation agents include quindine, Vitamin E ($\alpha$-tocopherol), lower alkanols, and $C_3$-$C_{26}$ fatty acids, most preferably long chain saturated and unsaturated fatty acids. Effective concentration ranges were found to be about 2 mg to 50 mg per 500 $\mu$ls of serum for the fatty acids and $\alpha$-tocopherol, 50 $\mu$g to 500 $\mu$g per 500 $\mu$ls of serum for quinidine, and 3 mg to 100 mg for a lower (saturated or unsaturated) alkanol ($C_2$-$C_7$) such as isopropyl alcohol.

Results obtained in experiments comprising adding $^3$H-digoxin to normal human serum following by the addition of a dissociating agent and centrifugal filtration are summarized below in Table 1.

TABLE 1

| Dissociating Agent | Mg Added/500 $\mu$ls Serum | % $^3$H—Digoxin Recovery in Filtrates |
|---|---|---|
| 1. H$_2$O | 10 | 81 |
| 2. Arachidonic Acid | 10 | 104 |
| 3. Linolenic Acid | 10 | 96 |
| 4. Vitamin E | 20 | 91 |
| 5. Quinidine | (200 $\mu$gs) | 87 |
| 6. Linoleic | 10 | 103 |
| 7. Oleic | 10 | 91 |
| 8. Isopropanol | 25 | 93 |
| 9. Linolenic (16 mg) and Isopropanol (9 mg) | 25 | 98 |

EXAMPLE

The use of a dissociating agent and centrifugal ultrafiltration is exemplified using a fluorescence polarization assay for digoxin on the COBAS BIO.

Reagents:
(1) Antibody Reagent—0.2 mole Tris(hydroxymethyl) aminomethane/liter, pH 8.0, containing rabbit anti-digoxin serum, 0.01% bovine gamma globulin, 0.1% sodium azide, and surfactant.
(2) Tracer Reagent—0.05 mole Tris(hydroxymethyl) aminomethane/liter, pH 8.0, containing 0.01% bovine gamma globulin 0.1% sodium azide, and surfactant.
(3) Digoxin Dissociating Agent—67% (v/v) of linolenic acid in isoproponol.

These reagents can be provided in kit form with one bottle of each reagent providing sufficient reagent quantities for multiple assays. The kit may also optionally contain one or more micropartition ultrafilters.

The assay is performed as follows:
(a) 500 $\mu$ls sample (serum, plasma, saliva, urine) are added to an Amicon Centrifree micropartition system filter (an anisotropic, hydrophilic YMT ultrafiltration membrane).
(b) 25 $\mu$ls of the digoxin dissociating agent are added and the contents of the filter are vortexed or mixed.
(c) After installing a collection cup on the bottom of the filter, the assembly is placed preferably in a fixed angle rotor (35°–45°) centrifuge and spun at 2000×g for 20 min.

(d) Following centrifugation, the filter and collection cup are removed from the centrifuge and the ultrafiltrate containing the digoxin is assayed in a fluorescence polarization assay to measure the digoxin concentration.

An example of a typical calibration curve is shown in FIG. 1.

We claim:

1. A method for determining total digoxin levels in a biological fluid sample containing digoxin-protein complex which method comprises disrupting the digoxin-protein complex by treating said sample solution with an effective amount of a dissociation agent selected from one or more members of the group consisting of a $C_3$-$C_{26}$ saturated or unsaturated fatty acid, a $C_{2-7}$ lower alkanol, quinidine and $\alpha$-tocopherol so as to release the bound digoxin from serum protein, passing the treated sample solution through a centrifugal ultrafilter so as to selectively pass digoxin containing sample solution through said filter and retaining said serum proteins and determining the digoxin contents in said sample solution in a fluorescence polarization assay.

2. The method of claim 1 wherein said dissociation agent is linolenic acid.

3. The method of claim 1 wherein said dissociation agent is arachadonic acid.

4. The method of claim 1 wherein said dissociation agent is linoleic acid.

5. The method of claim 1 wherein said dissociation agent is a mixture of isopropyl alcohol and linolenic acid.

6. The method of claim 1 wherein said dissociation agent is isopropyl alcohol.

7. A kit useful for determining total digoxin levels in a biological fluid sample, said kit comprising one bottle each of the following reagents in quantities sufficient to carry out multiple assays:
(1) anti-digoxin antibody reagent solution;
(2) Tracer reagent solution; and
(3) digoxin-protein complex dissociating agent solution.

8. The kit of claim 7 wherein said anti-digoxin antibody is rabbit anti-digoxin serum.

9. The kit of claim 7 wherein said digoxin-protein complex dissociating agent is a mixture of linolenic acid in isopropanol.

10. The kit of claim 7 wherein said tracer solution is a fluorescein digoxin conjugate.

11. The kit of claim 7 wherein
(1) said anti-digoxin antibody is rabbit anti-digoxin serum;
(2) said digoxin-protein complex dissociating agent is selected from the group consisting of linolenic acid, arachadonic acid and linoleic acid; and
(3) digoxin tracer reagent solution is a fluorescein digoxin conjugate.

* * * * *